(12) United States Patent
Akinsanya

(10) Patent No.: US 8,552,249 B2
(45) Date of Patent: Oct. 8, 2013

(54) MEDICATED DIAPER

(76) Inventor: Aderonke Akinsanya, Millbrook, AL (US)

(*) Notice: Subject to any disclaimer, the term of this patent is extended or adjusted under 35 U.S.C. 154(b) by 331 days.

(21) Appl. No.: 12/890,685

(22) Filed: Sep. 26, 2010

(65) Prior Publication Data
US 2012/0078211 A1    Mar. 29, 2012

(51) Int. Cl.
*A61F 13/15*    (2006.01)
(52) U.S. Cl.
USPC ............................ 604/360; 604/359; 604/364
(58) Field of Classification Search
USPC .......................................... 604/360, 359, 364
See application file for complete search history.

(56) References Cited

U.S. PATENT DOCUMENTS

| | | | | |
|---|---|---|---|---|
| 3,585,998 | A * | 6/1971 | Hayford et al. | 604/359 |
| 3,875,942 | A * | 4/1975 | Roberts et al. | 604/370 |
| 4,623,339 | A * | 11/1986 | Ciraldo et al. | 604/359 |
| 4,790,836 | A * | 12/1988 | Brecher | 604/359 |
| 7,491,863 | B2 * | 2/2009 | Odorzynski et al. | 604/359 |
| 7,858,840 | B2 * | 12/2010 | Hisanaka | 604/364 |
| 2002/0128615 | A1 * | 9/2002 | Tyrrell et al. | 604/364 |

* cited by examiner

*Primary Examiner* — Jacqueline F. Stephens
(74) *Attorney, Agent, or Firm* — The Law Office of Jerry D. Haynes

(57) ABSTRACT

An anti-rash diaper for preventing and treating diaper rash and skin irritations comprising: an absorbent layer, where the absorbent layer draws moisture; medicated ointment, where the ointment is applied over the absorbent layer; and a protective sheet, where the protective sheet is releasably attached over the ointment. The anti-rash diaper according to the present invention may further include elastic waistbands. A hook and loop fastener may be used to attach the protective sheet to the diaper. The protective sheet effectively secures the ointment over the absorbent layer.

3 Claims, 1 Drawing Sheet

MEDICATED DIAPER

BACKGROUND OF THE INVENTION

1. Field of Invention

The present invention relates to a diaper that includes a medicated ointment to reduce the likelihood of diaper rash or other skin irritations on the wearer thereof.

2. Description of Related Art

A diaper is an undergarment that is principally worn by infants who are not potty trained and some adults that may be incapable of controlling their bladder or bowel movements. Diapers come in various sizes and have been made of cloth and disposable materials. Cloth diapers are principally used with infants and are a traditional means of providing a diaper. Disposable diapers are more popular due to convenience and speed of clean up. Disposable diapers include non-woven polymer materials, resealable tapes, and elastic waistbands in order to secure the diaper in place. Many of the modern disposable diapers include multiple layers in order to transfer and distribute moisture into an absorbent core structure, therefore removing the moisture from the layer nearest the skin.

Diapers may include the tapes or Velcro to allow adjusting of the fit and in certain instances reapplication of an unsoiled diaper after confirmation that the diaper is not been soiled. Diapers may also include wetness indicators that provide a color change to indicate the presence of moisture in a diaper. Some disposable diapers include fragrances, lotions, oils or other scent masking substances in order to mask the scent of the diaper and in some instances to protect the skin. Nevertheless, the skin of an individual or infant who is wearing a diaper is subject to skin irritation, rash, dermitits, and other disorders. Diaper rash is a common form of irritation and affects the infant's skin that is covered with a diaper. The skin of the infant may become irritated over time even when using a diaper that has multiple layers. At certain instances a parent or caregiver may be unaware that the diaper needs changing, therefore the infant may remain in a soiled diaper for a substantial amount of time. This continued exposure to the waste specifically urine which includes by-products of ammonia and bacteria can cause severe skin rashes and irritation.

Some solutions that address the skin conditions related to diaper use include absorbent powders or super-absorbent materials within the diaper or the application of a topical cream ointment, lotion or paste onto the affected areas after the rash has developed. Some diapers include ointments or lotions within the absorbent area in an attempt to address or reduce the likelihood or spread of a diaper rash. U.S. Pat. No. 5,609,587 discloses a diaper containing a liquid pervious top sheet coated with a lotion composition where the lotion composition reduces the adherence of BM to the skin of the wearer, therefore improving the ease of BM cleanup and improves skin softness. U.S. Pat. No. 6,149,934 discloses an absorbent article having body side liner that includes a lotion formulation on the outer body facing surface. The lotion formulation acts as a lubricant to reduce the abrasion of the skin caused by the liner and transfers to the skin to provide an improved skin health.

SUMMARY OF THE INVENTION

The present invention relates to an anti-rash diaper for preventing and treating diaper rash and skin irritations comprising: an absorbent layer, where the absorbent layer draws moisture; medicated ointment, where the ointment is applied over the absorbent layer; and a protective sheet, where the protective sheet is releasably attached over the ointment. The anti-rash diaper according to the present invention may further include elastic waistbands. A hook and loop fastener may be used to attach the protective sheet to the diaper. The protective sheet effectively secures the ointment over the absorbent layer.

DETAIL DESCRIPTION

The present invention provides an anti-rash diaper where the diaper includes a medicated diaper rash ointment on the skin-contacting layer of the diaper. The application of this medicated ointment on the skin-contacting layer helps prevent diaper rash or can alleviate diaper rash that is present on the skin of an infant or a wearer. The ointment lies under a protective sheet that is used to cover the ointment when the diaper is packaged. The use of a protective sheet ensures that the ointment stays in place and is of a suitable consistency to be effective when placed on the infant.

Figure 1A:
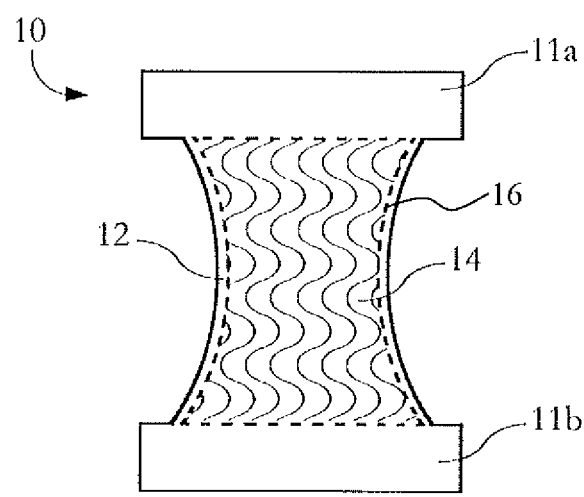
FIG. 1A depicts the top view of an anti-rash diaper according to the present invention.
Figure 1B:
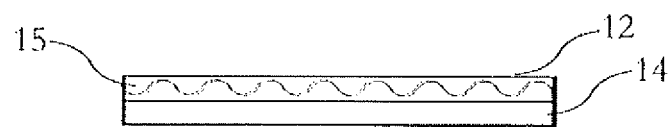
FIG. 1B shows a sectional view of the anti-rash diaper according to the present invention.

An anti-rash Diaper 10 is depicted in FIG. 1A. The anti-rash diaper 10 includes elastic waistbands 11a, 11b which are used to wrap and attach the diaper into place on an infant or adult. The center portion of the diaper, which is applied to the infant's or wearer's skin, includes an absorbent Layer 14 which is covered with an anti-rash Medicated Ointment 15. The anti-rash medicated ointment is applied over this skin contacting surface of the absorbent Layer 14. Over the anti-rash Ointment 15, a thin Protective Sheet 12 is applied that is used to secure the ointment over the layer and keep the ointment in a suitable consistency during packaging and before the diaper is used.

The use of the anti-rash Diaper 10 is especially effective for children that may have to attend day care where there is a likelihood that there may be inattentive caregiver who fails to effectively and timely change diapers to prevent the onset of diaper rash. The Protective Sheet 12 is attached to the diaper with a hook and loop fastener 16 therefore covering the entire surface of the Medicated Ointment 15. The hook and loop fastener 16, which follows along the dotted lin, attaches a peripheral edge of the Protective Sheet 12 to the center portion of the anti-rash diaper 10.

The anti-rash Diaper 10 according to present invention provides an improved diaper to prevent skin irritations and to alleviate diaper rash that may have developed on an infant's skin. The anti-rash diaper according to present invention is an innovative diaper that also prevents the use of hands to apply medicated ointment to the infant's skin area and therefore eliminates the use of hands and helps to diminish the irritation or pain the infant may be suffering due to the diaper rash. The anti-rash Diaper 10 also may be stored conveniently and packaged in a manner due to the use of the Protective Sheet 12 that covers the medicated ointment. Use of the anti-rash diaper 10 also makes the process of changing an infant's diaper quicker because it eliminates the necessity of applying ointment or diaper rash cream to the baby's skin.

What is claimed is:

1. An anti-rash diaper for preventing and treating diaper rash and skin irritations comprising:

a. an absorbent layer, where the absorbent layer draws moisture;

b. medicated ointment, where the ointment is applied over the absorbent layer;
c. a protective sheet, where the protective sheet is releasably attached over the ointment;
d. an elastic waistband, where the elastic waistband attaches the anti-rash diaper around a wearer; and
e. a hook and loop fastener, where the hook and loop fastener attaches the protective sheet to a center portion of the diaper.

2. The anti-rash diaper according to claim 1, where the protective sheet secures the ointment over the absorbent layer.

3. An anti-rash diaper for preventing and treating diaper rash and skin irritations comprising:
a. an absorbent layer, where the absorbent layer draws moisture;
b. medicated ointment, where the ointment is applied over the absorbent layer;
c. a protective sheet, where the protective sheet is releasably attached over the ointment;
d. an elastic waistband, where the elastic waistband attaches the anti-rash diaper around a wearer; and
e. a hook and loop fastener, where the hook and loop fastener attaches the protective sheet to the diaper and the hook and loop fastener is positioned around a peripheral edge of the protective sheet.

* * * * *